US007857833B2

(12) United States Patent
Abdou

(10) Patent No.: US 7,857,833 B2
(45) Date of Patent: Dec. 28, 2010

(54) DEVICES AND METHODS FOR INTER-VERTEBRAL ORTHOPEDIC DEVICE PLACEMENT

(76) Inventor: M. Samy Abdou, 7790 Doug Hill, San Diego, CA (US) 92127

( * ) Notice: Subject to any disclaimer, the term of this patent is extended or adjusted under 35 U.S.C. 154(b) by 567 days.

(21) Appl. No.: 11/544,471

(22) Filed: Oct. 6, 2006

(65) Prior Publication Data

US 2007/0093829 A1    Apr. 26, 2007

Related U.S. Application Data

(60) Provisional application No. 60/724,386, filed on Oct. 6, 2005, provisional application No. 60/751,772, filed on Dec. 19, 2005.

(51) Int. Cl.
*A61B 17/70* (2006.01)
(52) U.S. Cl. .................. 606/254; 606/257; 606/259
(58) Field of Classification Search ........... 606/246, 606/250–263, 279, 86 A; 228/182, 189, 228/254; 29/173, 436
See application file for complete search history.

(56) References Cited

U.S. PATENT DOCUMENTS

| 3,073,584 | A | * | 1/1963 | Troeger | 267/160 |
| 3,277,555 | A | * | 10/1966 | Kutash | 29/898.042 |
| 3,825,992 | A | * | 7/1974 | Troeger | 29/436 |
| 4,309,777 | A | * | 1/1982 | Patil | 623/17.13 |
| 4,655,629 | A | * | 4/1987 | Flaherty | 403/291 |
| 4,997,123 | A | * | 3/1991 | Backus et al. | 228/182 |
| 5,335,418 | A | * | 8/1994 | Krivec | 30/266 |
| 6,110,173 | A | | 8/2000 | Thomas | |
| 6,241,730 | B1 | * | 6/2001 | Alby | 606/256 |
| 6,283,967 | B1 | | 9/2001 | Troxell et al. | |
| 6,432,108 | B1 | | 8/2002 | Burgess et al. | |
| 6,736,817 | B2 | | 5/2004 | Troxell et al. | |
| 6,761,721 | B2 | | 7/2004 | Burgess et al. | |
| 6,811,567 | B2 | | 11/2004 | Reiley | |
| 6,945,975 | B2 | | 9/2005 | Dalton | |
| 7,137,986 | B2 | | 11/2006 | Troxell et al. | |
| 2003/0125742 | A1 | | 7/2003 | Yuan et al. | |
| 2004/0133207 | A1 | | 7/2004 | Abdou | |
| 2004/0158247 | A1 | | 8/2004 | Sitiso et al. | |

(Continued)

FOREIGN PATENT DOCUMENTS

WO    WO 2004/032726    4/2004

(Continued)

*Primary Examiner*—Eduardo C Robert
*Assistant Examiner*—Steven J Cotroneo
(74) *Attorney, Agent, or Firm*—Fred C. Hernandez; Mintz Levin Cohn Ferris Glovsky and Popeo P.C.

(57) ABSTRACT

Disclosed are devices and methods for the re-construction of the vertebral lamina after partial or complete laminectomy. Pursuant to an exemplary method, a first bone fastener is anchored to a vertebral bone. A second bone fastener is anchored to the same vertebral bone, wherein the first and second fasteners are located on opposite sides of the vertebral midline. A connector member is used to inter-connect the two bone fasteners and produce a prosthetic lamina.

Multiple embodiments of the lamina prosthesis are illustrated. These devices reconstruct the spinal canal, mark the position of the nerves at re-operation and provide a stable platform for the placement of additional spinal stabilization implants.

19 Claims, 14 Drawing Sheets

U.S. PATENT DOCUMENTS

| | | |
|---|---|---|
| 2004/0204713 A1 | 10/2004 | Abdou |
| 2005/0004573 A1 | 1/2005 | Abdou |
| 2005/0177163 A1 | 8/2005 | Abdou |
| 2005/0177164 A1 * | 8/2005 | Walters et al. ............ 606/72 |
| 2005/0273120 A1 | 12/2005 | Abdou |
| 2005/0288669 A1 | 12/2005 | Abdou |
| 2005/0288670 A1 * | 12/2005 | Panjabi et al. ............ 606/61 |
| 2006/0052872 A1 * | 3/2006 | Studer et al. ............ 623/17.13 |
| 2006/0074488 A1 | 4/2006 | Abdou |
| 2006/0149278 A1 | 7/2006 | Abdou |
| 2006/0161154 A1 | 7/2006 | McAfee |
| 2006/0217710 A1 | 9/2006 | Abdou |
| 2006/0217719 A1 | 9/2006 | Albert et al. |
| 2006/0229615 A1 | 10/2006 | Abdou |
| 2007/0093828 A1 | 4/2007 | Abdou |
| 2007/0106383 A1 | 5/2007 | Abdou |
| 2007/0123884 A1 | 5/2007 | Abdou |

FOREIGN PATENT DOCUMENTS

| | | |
|---|---|---|
| WO | WO 2004/062482 | 7/2004 |
| WO | WO 2004/084774 A1 * | 10/2004 |
| WO | WO 2004/093702 | 11/2004 |
| WO | WO 2005/122922 | 12/2005 |
| WO | 2006/041963 | 4/2006 |
| WO | 2006/058221 | 6/2006 |
| WO | WO 2006/089292 | 8/2006 |
| WO | WO 2006/096756 | 9/2006 |
| WO | WO 2007/041648 | 4/2007 |
| WO | WO 2007/044705 | 4/2007 |
| WO | WO 2007/044836 | 4/2007 |
| WO | WO 2007/056516 | 5/2007 |
| WO | WO 2007/059207 | 5/2007 |

* cited by examiner

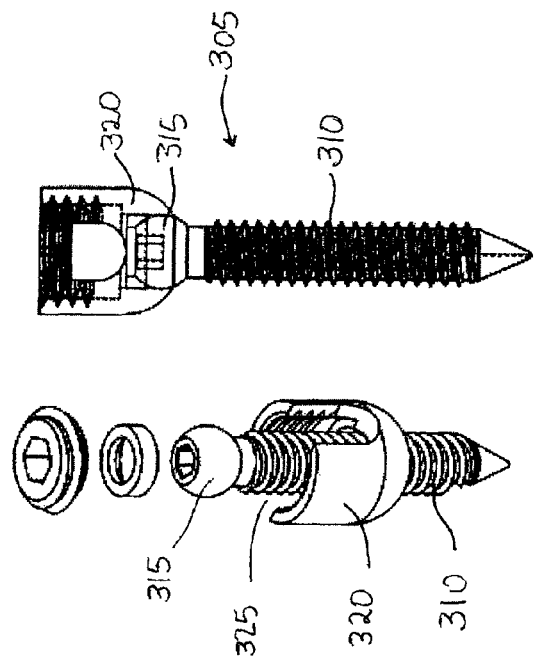
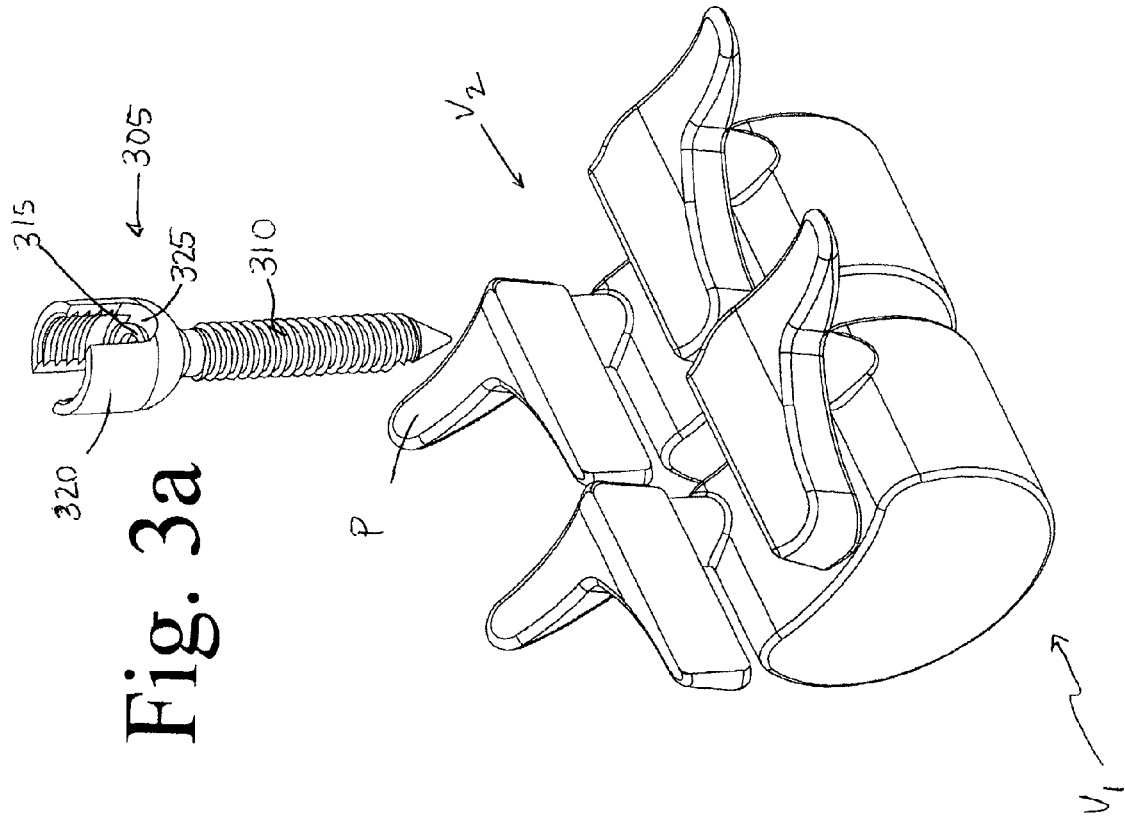
Fig. 3b
Fig. 3a

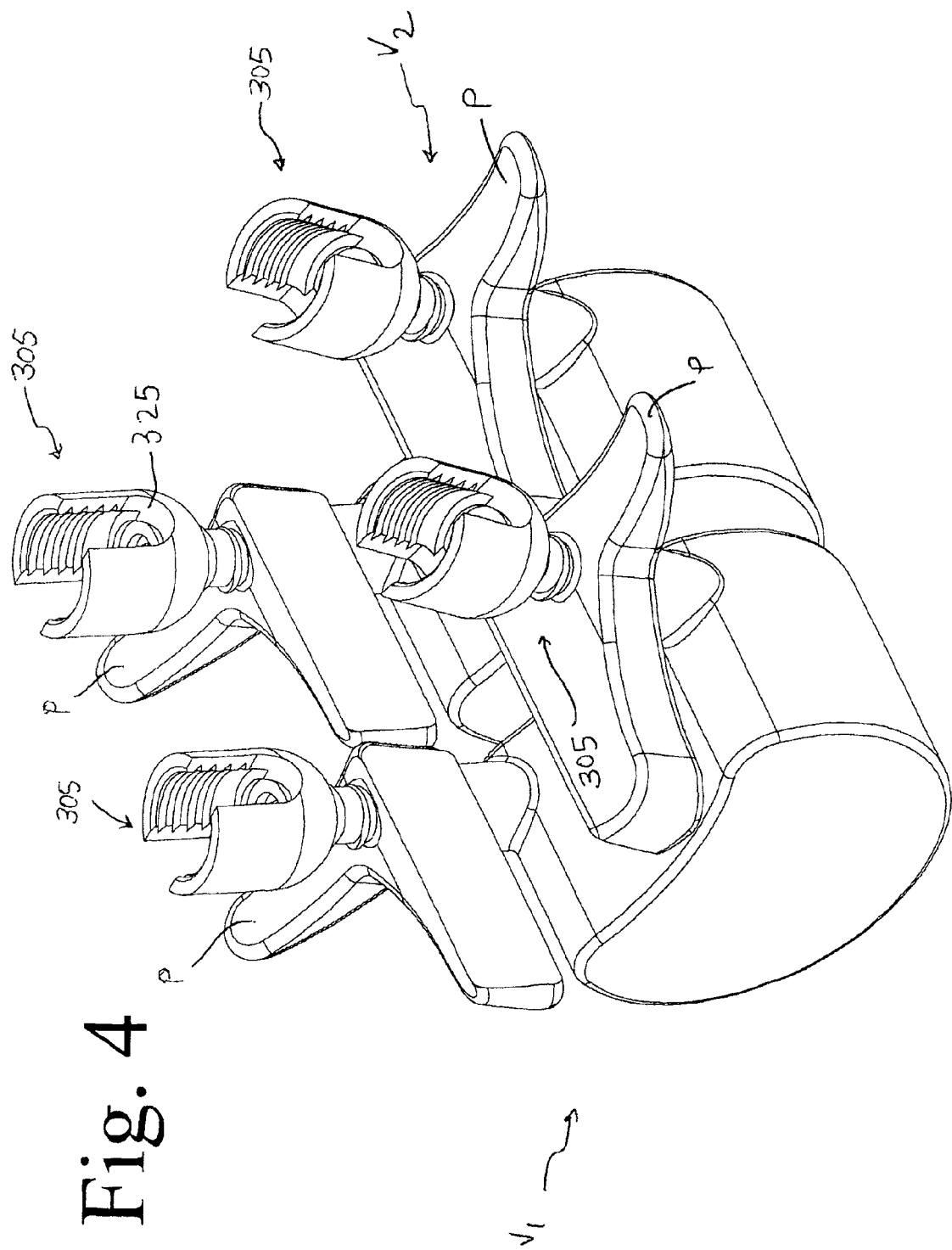

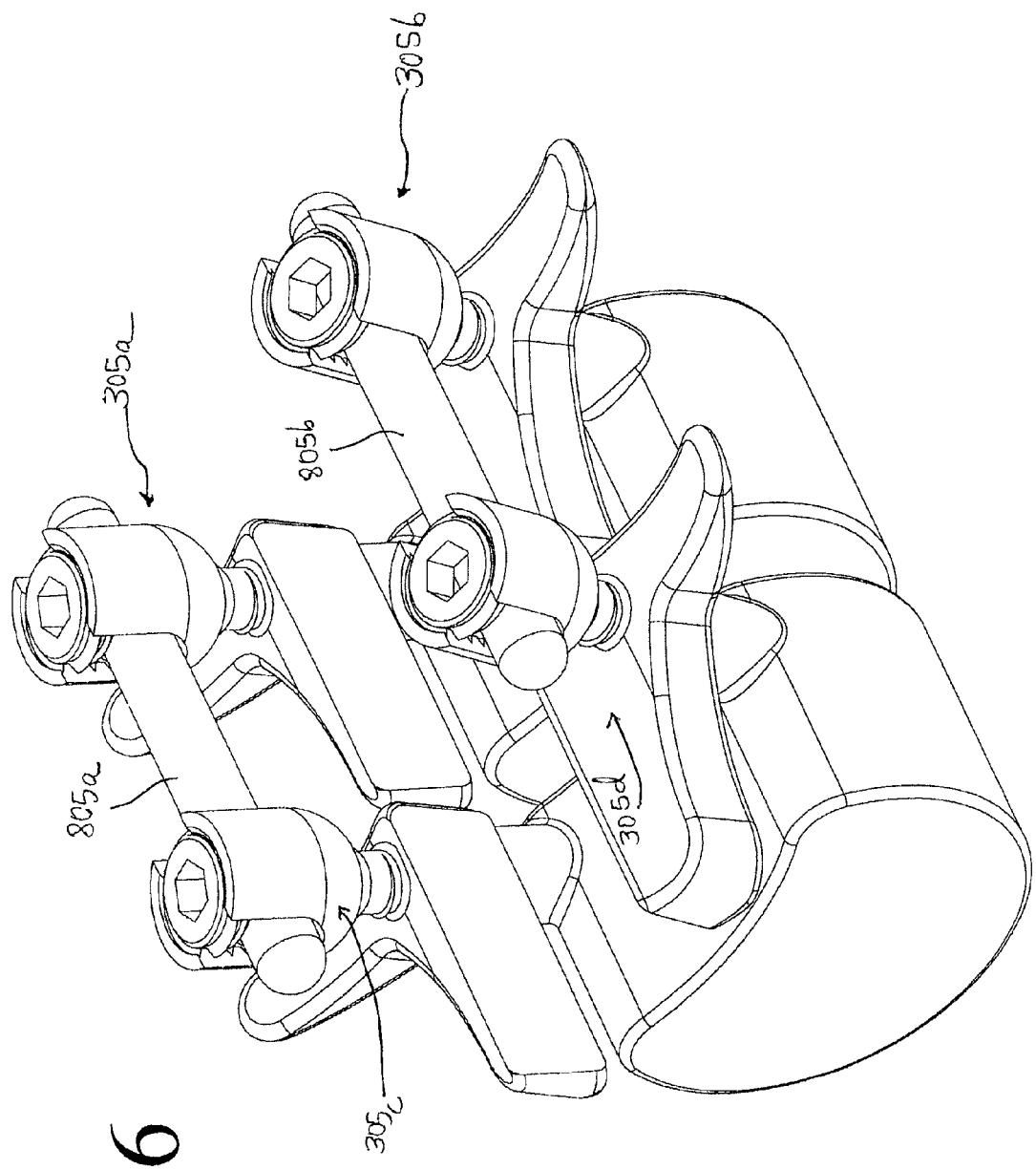

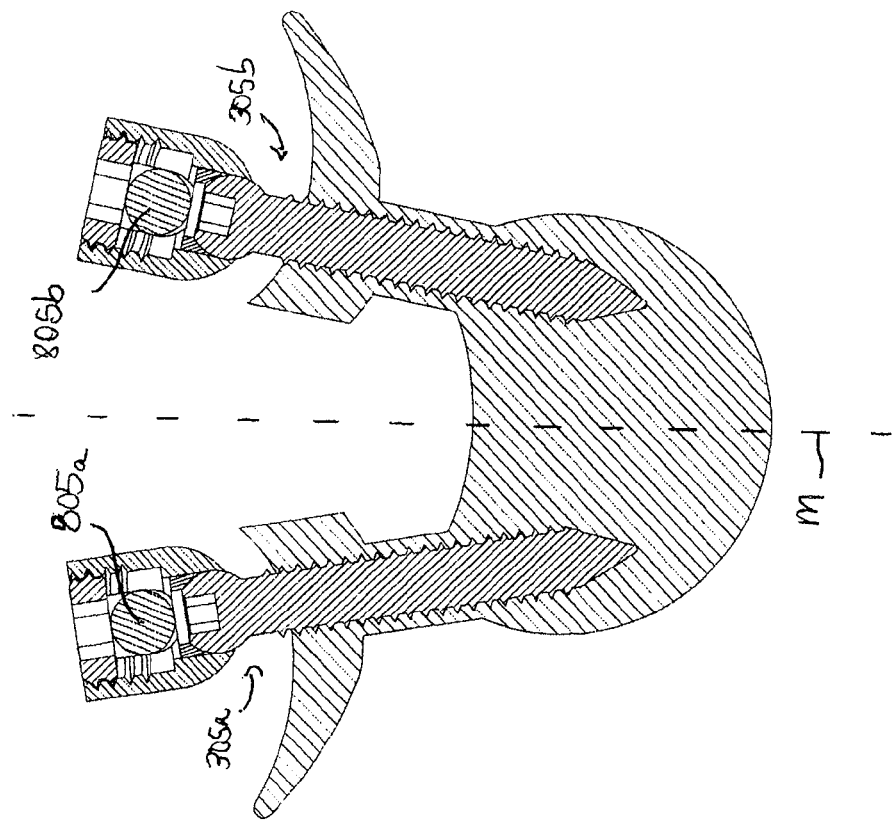
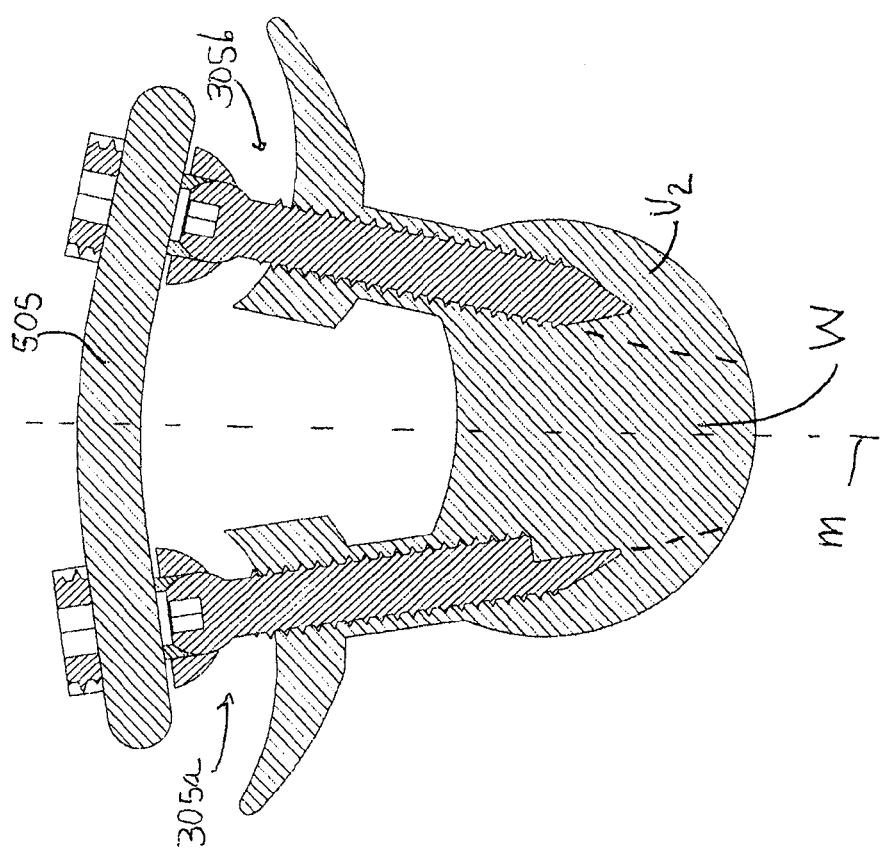

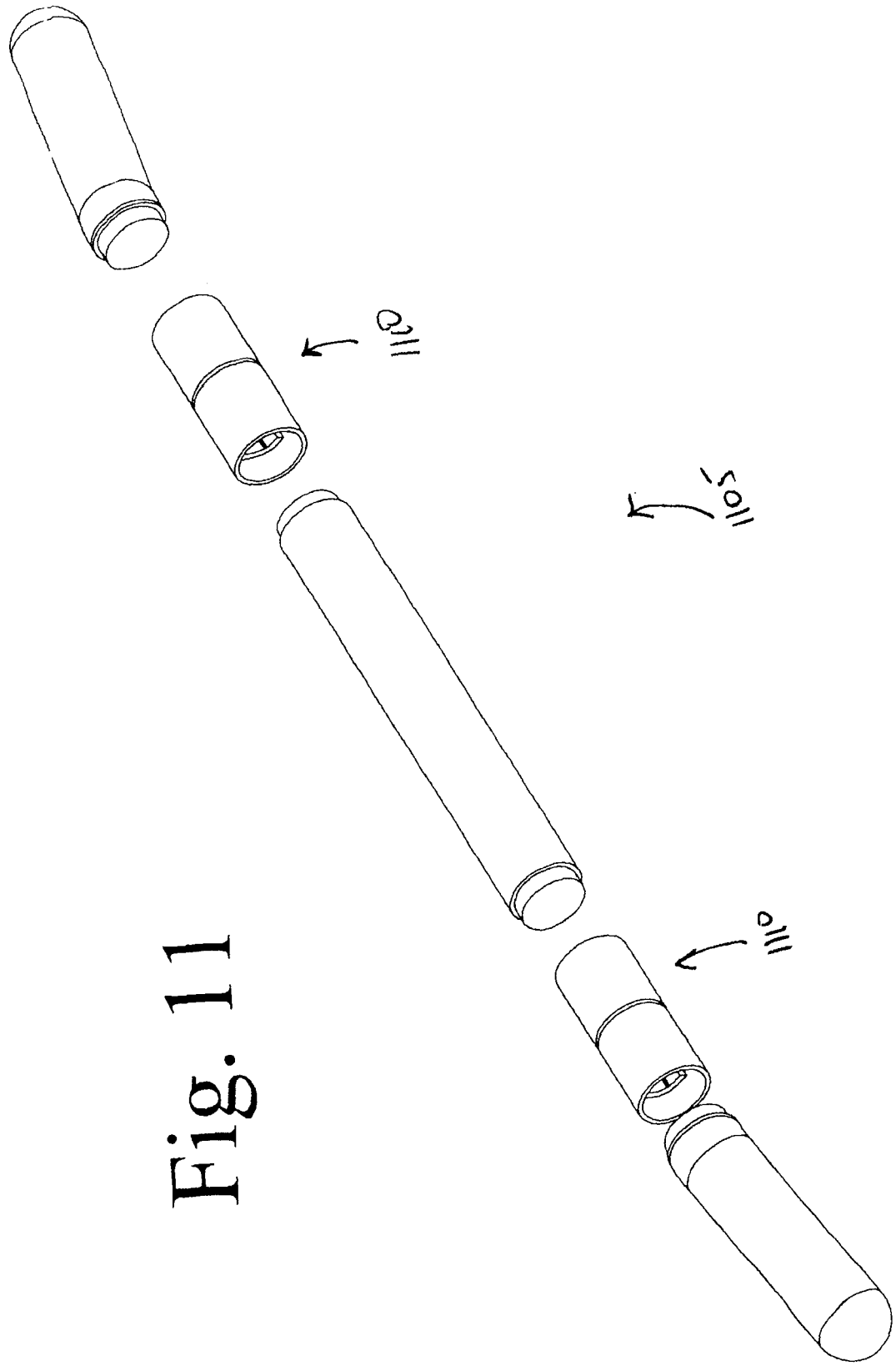

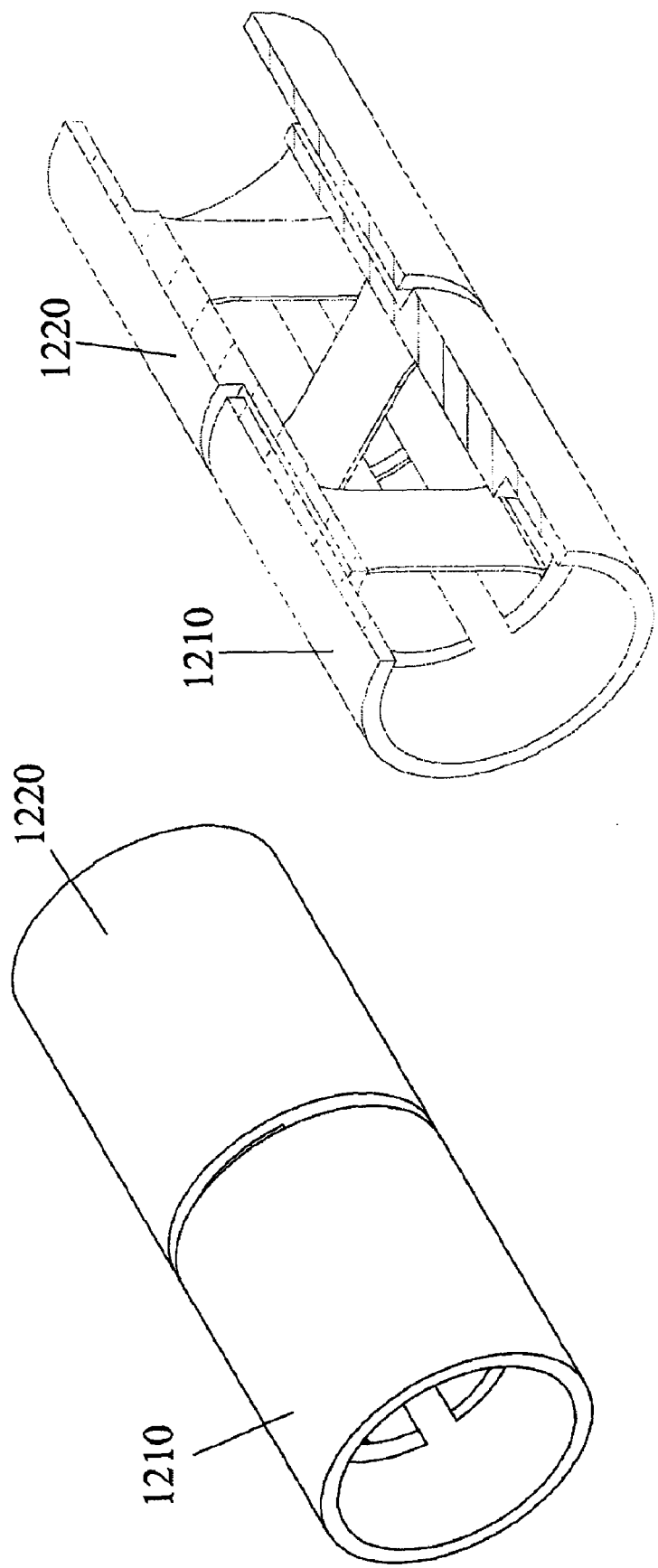

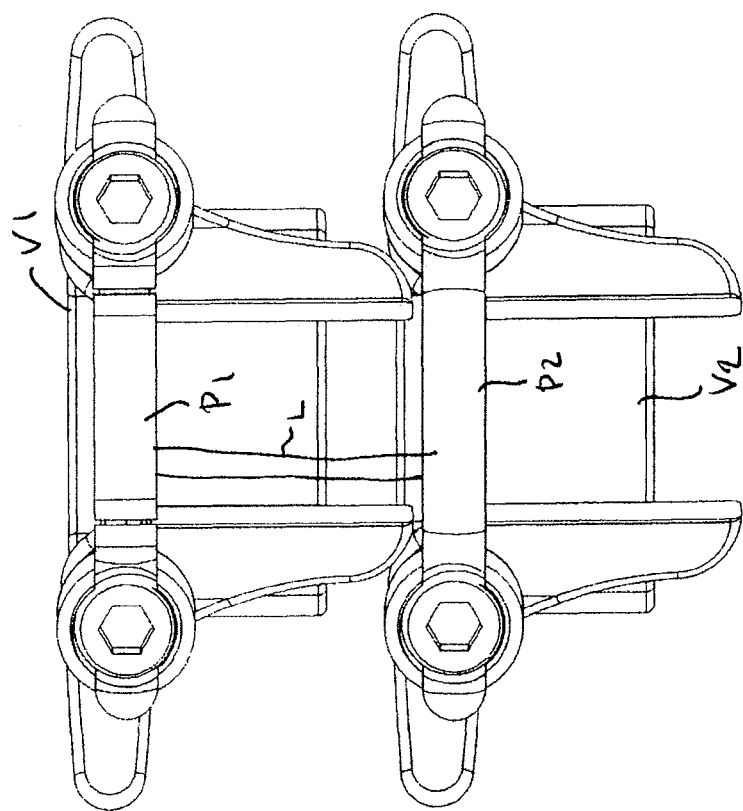
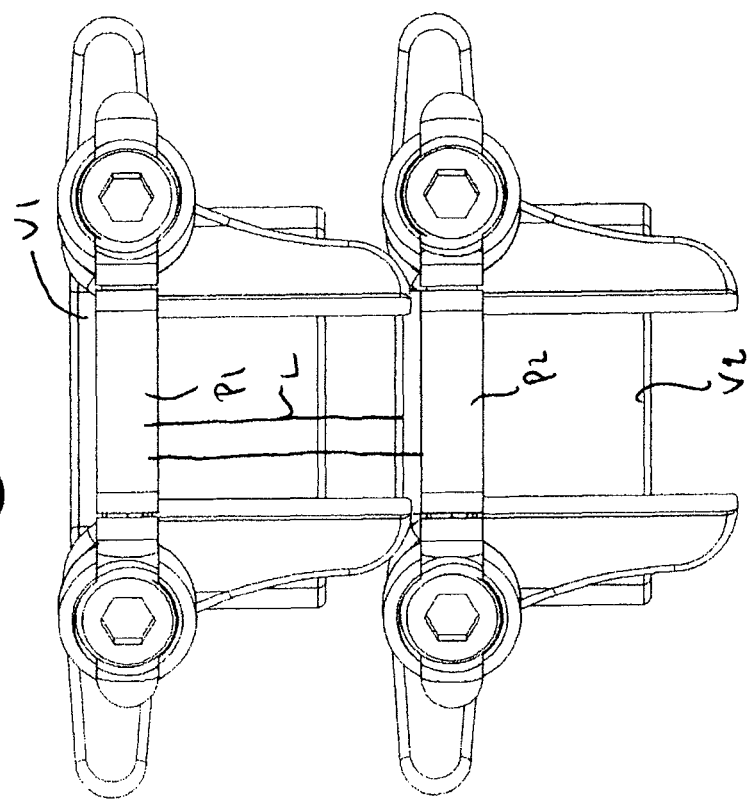

US 7,857,833 B2

DEVICES AND METHODS FOR INTER-VERTEBRAL ORTHOPEDIC DEVICE PLACEMENT

REFERENCE TO PRIORITY DOCUMENT

This application claims priority of co-pending U.S. Provisional Patent Application Ser. No. 60/724,386, filed Oct. 6, 2005 and U.S. Provisional Patent Application Ser. No. 60/751,772, filed Dec. 19, 2005. Priority of the aforementioned filing dates is hereby claimed and the disclosures of the Provisional Patent Applications are hereby incorporated by reference in their entirety.

This application also is related to International application Serial No. PCT/US2006/39822, filed the same day herewith.

Where permitted, the subject matter of each of the above noted provisional application and international application is incorporated by reference in its entirety by reference thereto.

BACKGROUND

The central hole within a vertebra is termed the spinal canal and it houses and protects the spinal cord and/or spinal nerves. Whether from degenerative disease, traumatic disruption, infection or neoplastic invasion, the spinal canal may become narrowed over one or more vertebral levels and lead to compression of the indwelling neural tissues. Narrowing of the spinal canal is termed spinal stenosis and this condition can produce significant pain, neurologic dysfunction and disability. In addition, mal-alignment of adjacent spinal vertebrae can further narrow the spinal canal and cause additional pain and disability.

The current surgical treatment of spinal stenosis is decompression of the neural tissues by removal of the bone and ligament elements that produce nerve compression. Laminectomy, the removal of the lamina segment of the vertebrae, is the most common way to achieve decompression of the spinal canal and hundreds of thousands of patients undergo this operation every year in the United States alone. Although the operation provides nerve decompression, it also has negative and permanent side-effects upon the spinal segments.

Laminectomy removes one side of the nerve's natural bony housing and leaves the posterior aspect of the neural tissues exposed and unprotected. The exposed nerves are vulnerable to injury and this vulnerability is especially problematic if future surgery is required. At the time of re-operation, the nerves have no posterior bony covering that can be used as a marker of nerve location. In addition, the dural sac that naturally encases the nerves will invariably scar onto the surrounding soft tissues thereby obscuring the tissue layers and making the exact position of the nerves unknown to the operating surgeon. This makes the dural sac and contained nerves particularly vulnerable to inadvertent injury during subsequent surgery and a dural injury rate of 10-20% rate has been reported at the time of re-operation. These dural violations can lead to permanent nerve injury, disability and chronic pain.

Laminectomy produces a defect in the bone and ligament structures that ensure the longitudinal alignment of adjacent vertebra and weakens the structural integrity of the spine. Many patents that undergo laminectomy will subsequently develop spinal instability and disabling pain. To treat the instability, various devices have been developed to support the spine. While some of these devices permit motion, others promote fusion and complete immobilization of the unstable spinal segments. Regardless of the specifics of design or function, these devices are anchored onto the vertebral bodies with bone screws or similar fasteners and will require a stable attachment platform onto which they may be affixed.

The stability of the attachment platform is critical to the proper function of the implant and those devices that are poorly anchored to the underlying bone will inevitably loosen with repeated vertebral movement. Solid device attachment is especially important in the implantation of devices that preserve vertebral motion. While fusion devices bear load until the bone has fused, motion preservation implants must provide indefinite support of the vertebral movement. As motion preservation implants are used with increasing frequency, there is a growing need for an improved method of attachment onto the underlying vertebral bone.

SUMMARY

Devices and methods are disclosed to address the above-described shortcomings of spinal canal decompression. The illustrated embodiments reconstruct the vertebrae after partial or complete removal of the lamina bone. They restore the integrity of the vertebral arch and provide a stable platform onto which additional implants may be attached. Those additional implants permit re-stabilization of the spinal segments that have been rendered unstable by disease or as a consequence of prior surgery. They include devices that promote bony fusion and complete spinal immobilization as well as devices that preserve motion between different spinal segments.

In one embodiment, a rod is used to connect two or more bone screws that are placed within the same vertebra but on opposite sides of the vertebral midline. This reconstructs the vertebral ring and marks the position of the nerves at re-operation. It also provides a stable platform for the subsequent attachment of additional devices. Since the rod connects two screws within the same vertebra, the rod is prevented from rotating relative to the anchoring vertebra. This method provides exceptional rotational stability and it is a significant improvement over the current techniques. Further, since the screws are affixed to the vertebrae using non-parallel trajectories, the screws can not be dislodged without the avulsion of the large bone wedge contained between them. These two factors synergistically increase the pull-out resistance of the screw/rod complex and significantly increase the stability of the attachment platform.

Additional embodiments of the rod are illustrated and some of those embodiments contain additional points of articulation. The latter minimizes the need for rod contouring at the time of surgery and expedites the procedure. Embodiments of a rigid inter-connecting rod with a mobile segment are also disclosed. These embodiments are particularly applicable in anchoring devices that stabilize the spinal segments while preserving spinal.

The varied embodiments disclosed in this application provide devices and methods that reconstruct the posterior ring of the vertebrae after complete or partial laminectomy. They cover and protect the underlying neural tissues and provide a reliable marker of nerve position during re-operation. The disclosed screw/rod arrangements also provide a very stable platform onto which additional spinal stabilization implants may be affixed. Finally, a method for the stabilization and preservation of spinal motion in even grossly unstable spinal segments is also presented.

In one aspect, there is disclosed a device for the reconstruction of vertebral lamina after at least partial laminectomy, comprising: a first fastener and a second fastener attached at one end onto a posterior aspect of a vertebra wherein the fasteners are positioned on opposite sides of the vertebral midline; a connector attached to another end of each fastener and adapted to transition between a first and second state, wherein the connector and fastener are freely movable relative to one another in a first state and immobilized relative to one another in a second state; and a rod that is adapted to attach onto one connector and fastener at one end and a second connector and fastener at another end, wherein the body of the rod crosses the vertebral midline.

In another aspect, there is disclosed a device for the reconstruction of vertebral lamina after at least partial laminectomy, comprising: a first fastener and a second fastener attached at one end onto a posterior aspect of a vertebra wherein the fasteners are positioned on opposite sides of the vertebral midline; a connector attached to another end of each fastener and adapted to transition between a first and second state, wherein the connector and fastener are freely movable relative to one another in a first state and immobilized relative to one another in a second state; a first rod that is adapted to attach onto a first connector and fastener at one end and a housing at another end; a second rod that is adapted to attach onto a second connector and fastener at one end and the housing at another end; wherein the housing is adapted to transition between a first state and a second state, wherein the end of each rod that interacts with the housing is freely movable relative to the housing in the first state and immobilized relative to the housing in the second state.

In another aspect, there is disclosed a method for stabilizing a first bone fastener is attached to the posterior aspect of a vertebral body that has undergone a laminectomy, comprising attaching the first bone fastener to at least one additional bone fastener that is anchored onto the same vertebral body, wherein at least one of the additional anchors is on an opposite side of the vertebral midline with respect to the first bone fastener.

In another aspect, there is disclosed a method of connecting adjacent vertebral bodies, comprising: positioning an interconnecting member so that the interconnecting member crosses the vertebral midline; and attaching the interconnecting member to first and second bone fasteners, wherein the first and second bone fasteners are anchored into the posterior aspect of vertebral bone that have had a partial or complete lamenectomy.

Other features and advantages will be apparent from the following description of various embodiments, which illustrate, by way of example, the principles of the disclosed devices and methods.

BRIEF DESCRIPTION OF THE DRAWINGS

FIG. 3A shows a pedicle screw being inserted into a pedicle segment P of the vertebral body V2.

FIG. 3B shows an exemplary embodiment of a pedicle screw.

FIG. 4 shows a pedicle screw anchored into each pedicle segment P of the vertebral bodies V1 and V2.

FIG. 6 shows a conventional method of vertebral immobilization

FIG. 7A shows a cross sectional view of the screw/rod configuration of FIG. 5.

FIG. 7B shows a cross sectional view of the screw/rod configuration of FIG. 6.

FIG. 11 shows another embodiment of an articulating rod in an exploded state.

FIGS. 12A and 12B show an articulating member of the rod.

FIGS. 15A and 15B shows articulating rods of FIGS. 11 and 13 being used to interconnect the screws on each side of the midline of the same vertebral bodies

DETAILED DESCRIPTION

Figure 1:
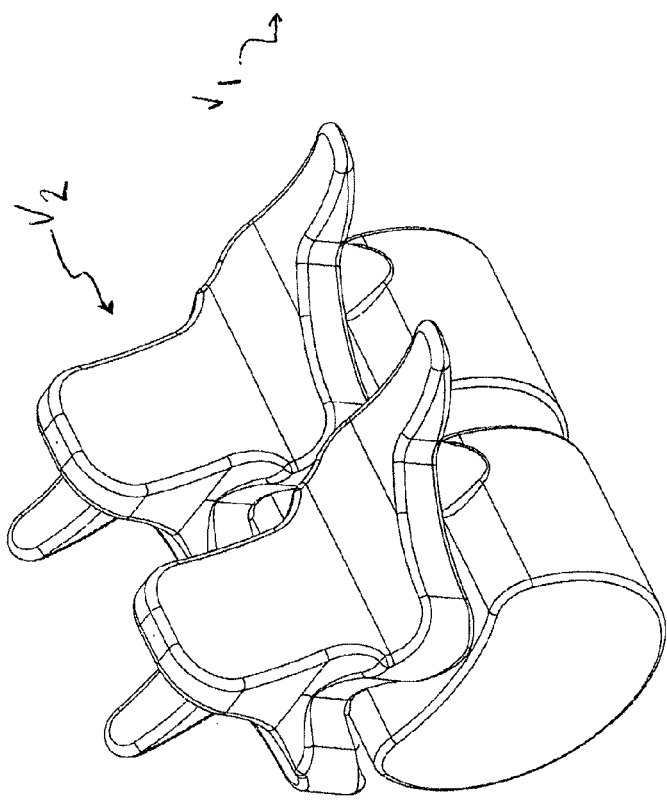
FIG. 1 shows two intact vertebral bodies V1 and V2.

FIG. 1 shows two intact vertebral bodies V1 and V2. For clarity of illustration, the vertebral bodies are represented schematically and those skilled in the art will appreciate that actual vertebral bodies include anatomical details not shown in FIG. 1. For clarity of illustration, certain anatomical details, such as the patient's skin, are not shown in at least some of the figures. The vertebral arch is comprised of two pedicles, the short stout processes that extend from the sides of the vertebral body and two laminae, the broad flat plates that project from the pedicles and join in a triangle to form a hollow archway (the foramen).

Figure 2:
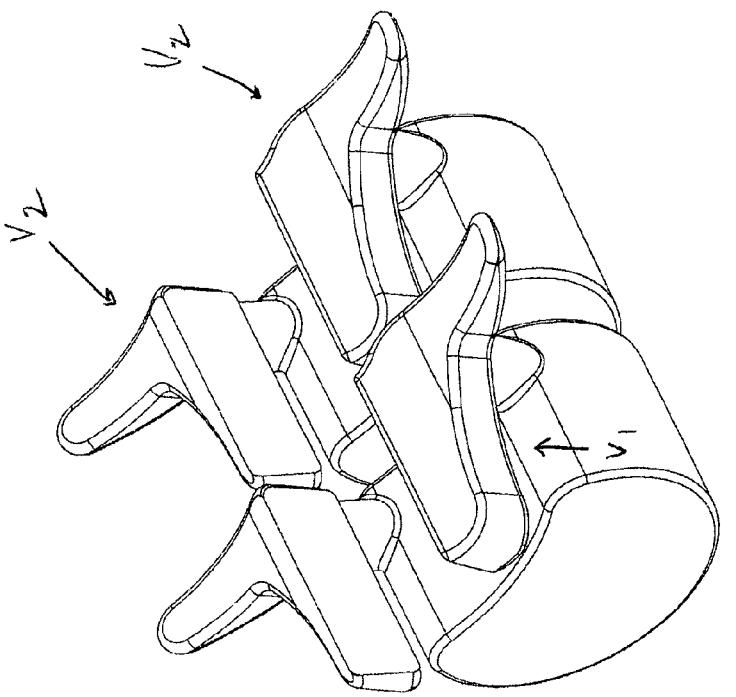
FIG. 2 illustrates the same vertebral bodies V1 and V2 after surgical resection of the lamina.

FIG. 2 illustrates the same vertebral bodies V1 and V2 after surgical resection of the lamina. The negative effects of laminectomy can be countered by the reconstruction of the lamina. With reference to FIG. 3a, a pedicle screw 305 is inserted into a pedicle segment P of the vertebral body V2. The pedicle screw 305 is shown in FIG. 3b and generally includes a shank 310 with a head 315 that is removably mounted in a housing or receiver 320 in a polyaxial configuration. The receiver 320 includes means, such as slots 325, adapted to receive an elongate stabilizer, or interconnecting member, such as a rod. It should be appreciated that the structure and type of pedicle screw can vary. As shown in FIG. 4, a pedicle screw 305 can be inserted into each pedicle segment P of the vertebral bodies V1 and V2.

Figure 5:
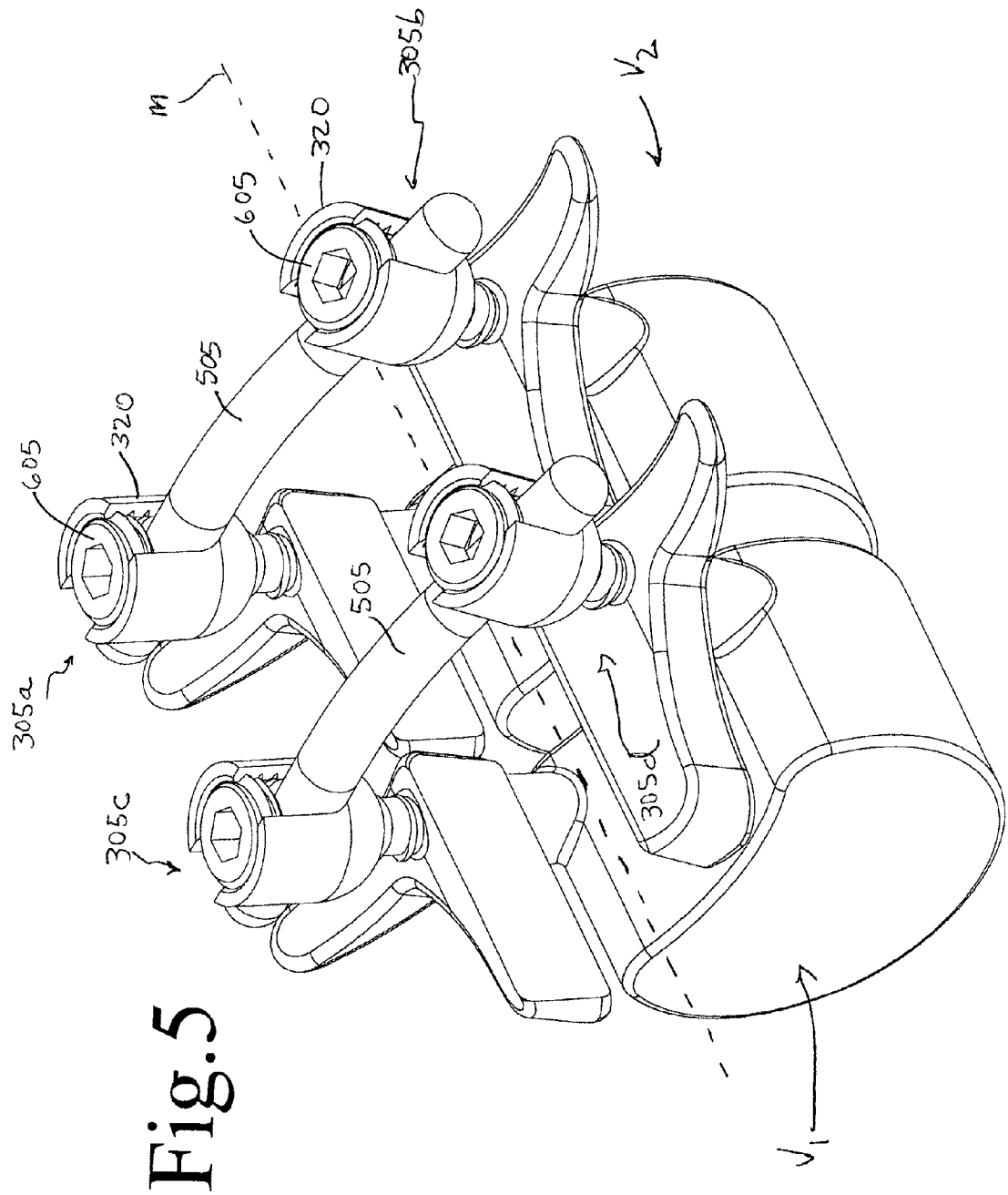
FIG. 5 shows a rod that is used to interconnect the screws on each side of the midline of the same vertebral body V2.

FIG. 5 shows a rod 505 that is used to interconnect the screws 305a and 305b on opposite sides of the vertebral midline M of the same vertebral body V2. The rod 505 is lowered into the receiver 320 of each screw. A locking means, such a locking nut 605 secures the rod to the receiver 320. The screws 305c and 305d on each side of the midline of the same vertebral body V1 can also be interconnected by another rod 505. A rod 505 connects the screws 305a and 305b on the vertebral body V2 and a rod 505 connects the screws 305c and 305d on the vertebral body V1. As demonstrated, the device reforms the posterior border of the neural canal and protects the nerves within it. It also provides a marker of nerve location at re-operation.

In the illustrated construct, the two rods 505 can also serve as an attachment platform for devices that realign and stabilize the spine. Depending on the specifics of the design, these devices may function to preserve spinal motion or immobilize the two vertebral bodies. FIG. 6 shows a conventional method of vertebral immobilization. In the construct of FIG. 6, a rod 805a is used to connect the screws 305a and 305c of the two vertebral bodies, the rod 805a being positioned on a single side of the midline. A rod 805b is used to connect the screws 305b and 305d of the two vertebral bodies, the rod 805b being positioned on a single side of the midline. Using the method construct of FIG. 6, the screws 305 have no rotational stability since each screw is anchored in a different vertebral body and each screw may rotate freely relative to its anchor site.

FIG. 7A shows a cross sectional view of the screw/rod configuration of FIG. 5, while FIG. 7B shows a cross sectional view of the screw/rod configuration of FIG. 6. As shown in FIG. 7A, interconnection of the screws on each or opposite sides of the vertebral midline M reconstructs the posterior aspect of the spinal canal and produces a platform with exceptional rotational stability. Further, the pull-out resistance of the screws 305 is also enhanced since the interconnected screws 305 capture a wedge W of bone between them. The wedge W must be avulsed before the screws can dislodge thereby providing greater pull-out resistance for the screws than the configuration of FIG. 7B. By contrast, the interconnected screws connected by the method of FIGS. 6 and 7B do not capture a wedge of bone and are completely dependent on thread purchase to resist pull-out.

Figure 8B:
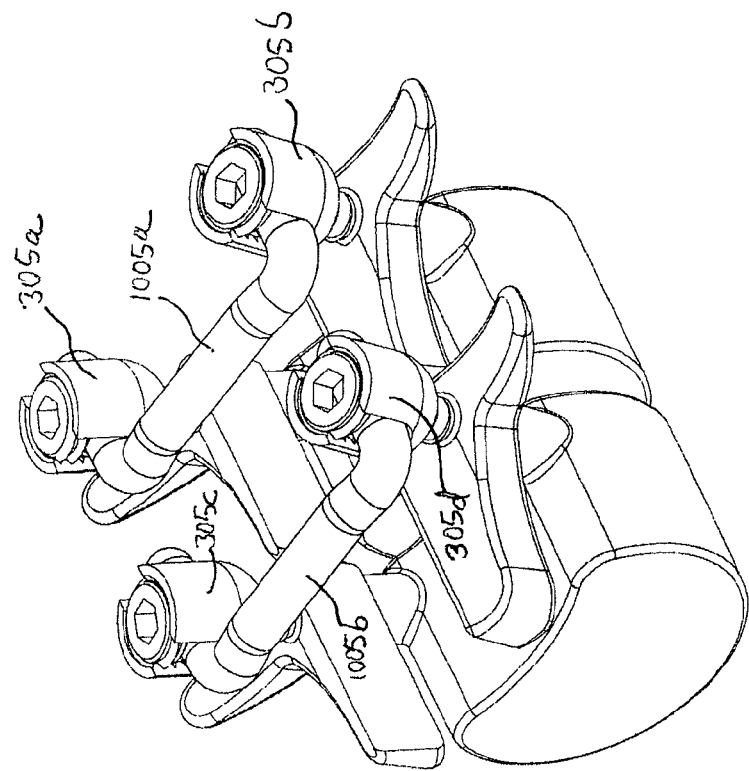
FIGS. 8A and 8B show alternative embodiments of a rod that interconnects a set of screws on opposite sides of the midline of the same vertebral body.
Figure 8A:
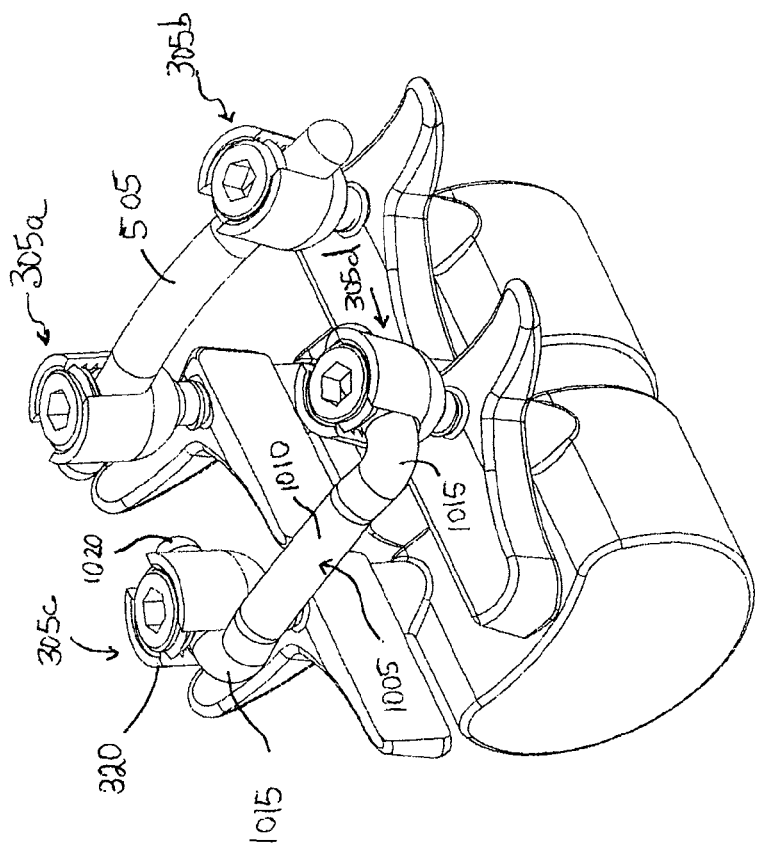

FIG. 8A shows an alternative embodiment of a rod 1005 that can be used to interconnect a set of screws 305c and 305d on opposite sides of the midline of the same vertebral body. In FIG. 8A, rod 1005 interconnects screws 305c and 305d while a straight rod 505 connects the screws 305a and 305b. The rod 1005 includes a central section 1010 that passes over the midline, a pair of bends 1015, and a pair of coupling sections 1020 transverse to the central section 1010 that couple to the receiver members 320 of the screws 305. Use of the rod 1005 provides increased space between the upper rod 505 and the lower rod 1005 and permits use of a longer/larger device to connect them. FIG. 8B shows a first rod 1005a interconnecting screws 305a/305b and a second rod 1005b interconnecting screws 305c/305d. This configuration shown allows the center point of a device used to connect the two rods 1005 to substantially match the position of the disc space. This is particularly useful when using a device that preserves segmental motion since the device may now be centered on the axis of rotation of the disc space and vertebral bodies.

Figure 9:
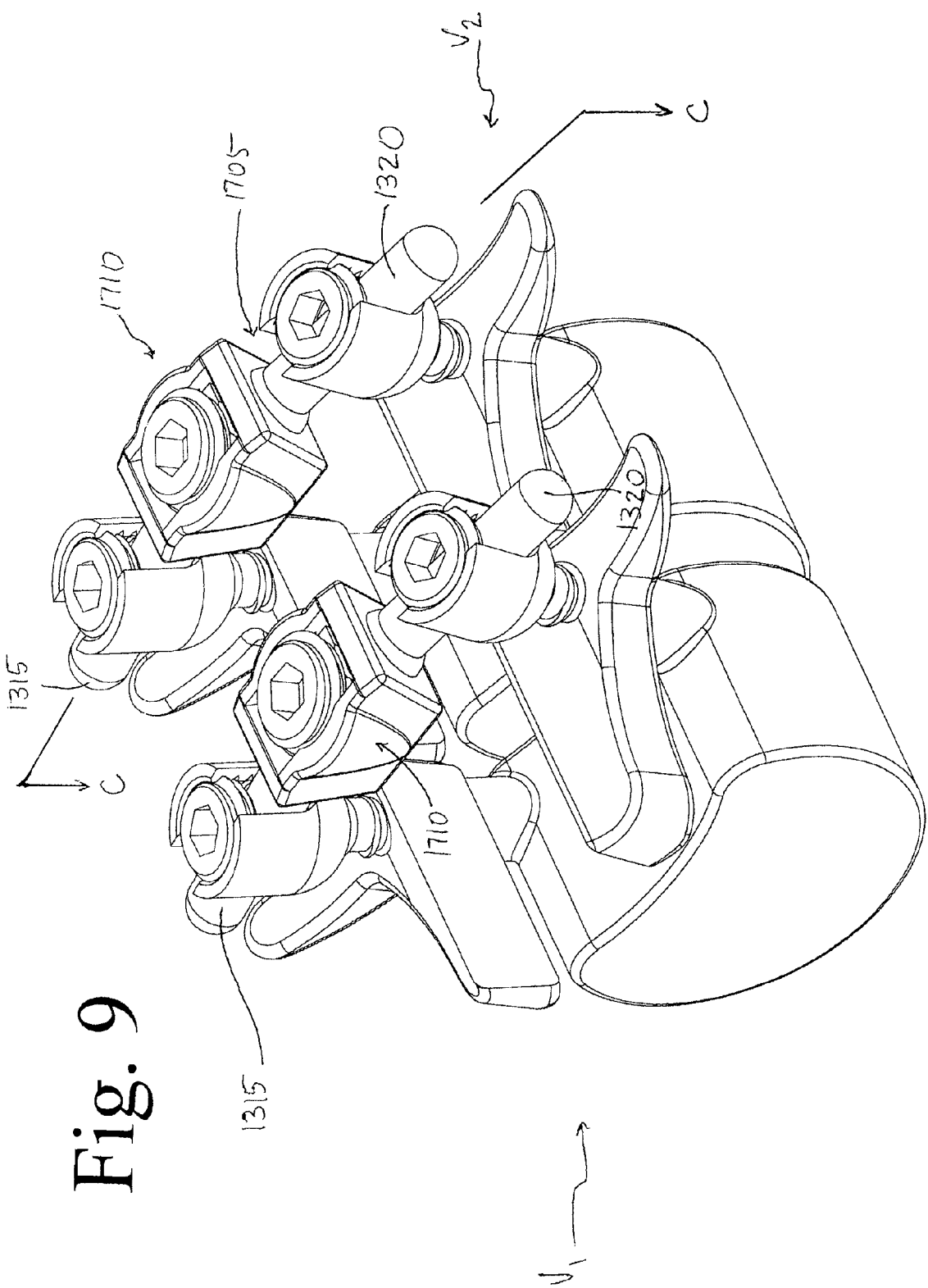
FIG. 9 shows an alternative embodiment of an articulating rod that interconnects screws on either side of the midline on the same vertebral body.
Figure 10C:
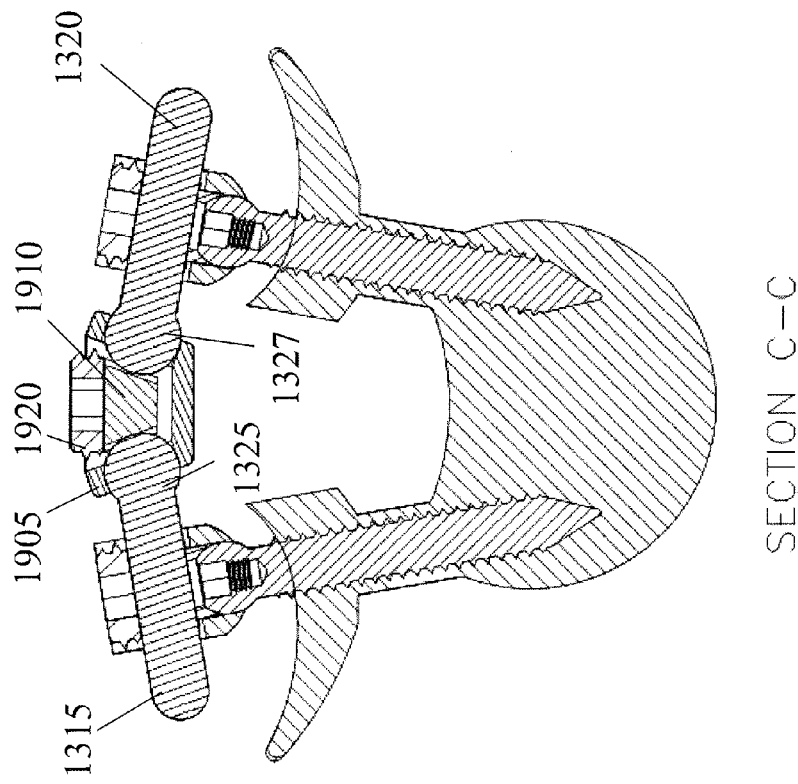
FIG. 10C shows a cross-sectional view of the articulating rod attached to screws on the vertebral body V2.
Figure 10A:
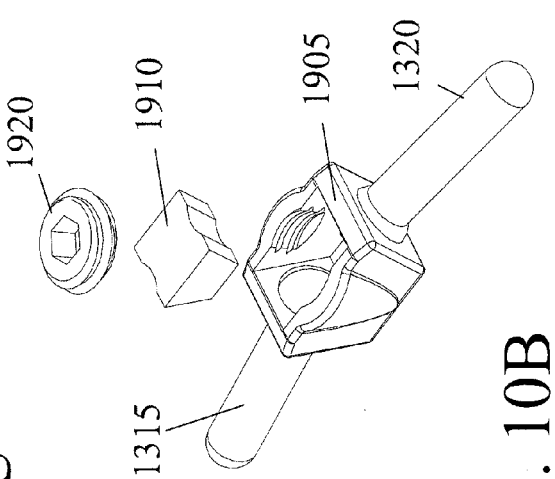
FIG. 10A shows a perspective, exploded view of the articulating rod.
Figure 10B:
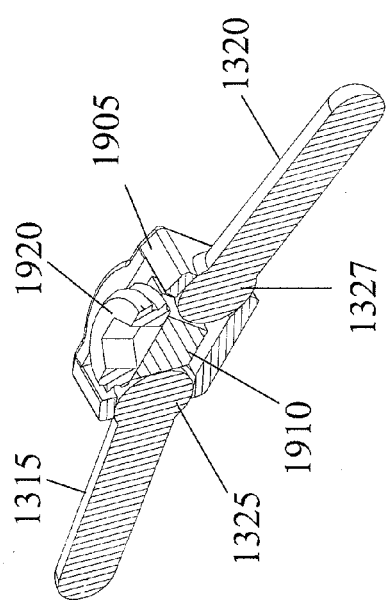
FIG. 10B shows a cross-sectional view of the articulating rod.

FIG. 9 shows an embodiment of an inter-connecting rod 1705 that contains additional points of articulation mechanism. The articulation mechanism 1710 permits the first rod section 1315 of the rod 1705 to articulate and rotate relative to the second rod section 1320. FIG. 10A shows component members of the device while FIG. 10B shows a cross-sectional view of the rod 1705. FIG. 10C shows a perspective, cross-sectional view of the assembled construct. The articulation member 1710 includes a housing 1905 that couples to the first rod section 1315 and the second rod section 1320 in a ball-and-socket configuration. That is, the ends 1325, 1327 of the first and second rod sections each have ball shapes that are rotatingly positioned inside the housing 1905. A locking member 1910 can be compressed downward onto the ball-ends 1325, 1327 of the first and second rod sections to lock the position and orientation of the first and second rod sections 1315, 1320 relative to the housing 1905. A set screw 1920 has threads that mate with threads on the housing 1905. The set screw 1920 is tightened downward to compress and lock the locking member 1910.

Figure 13:
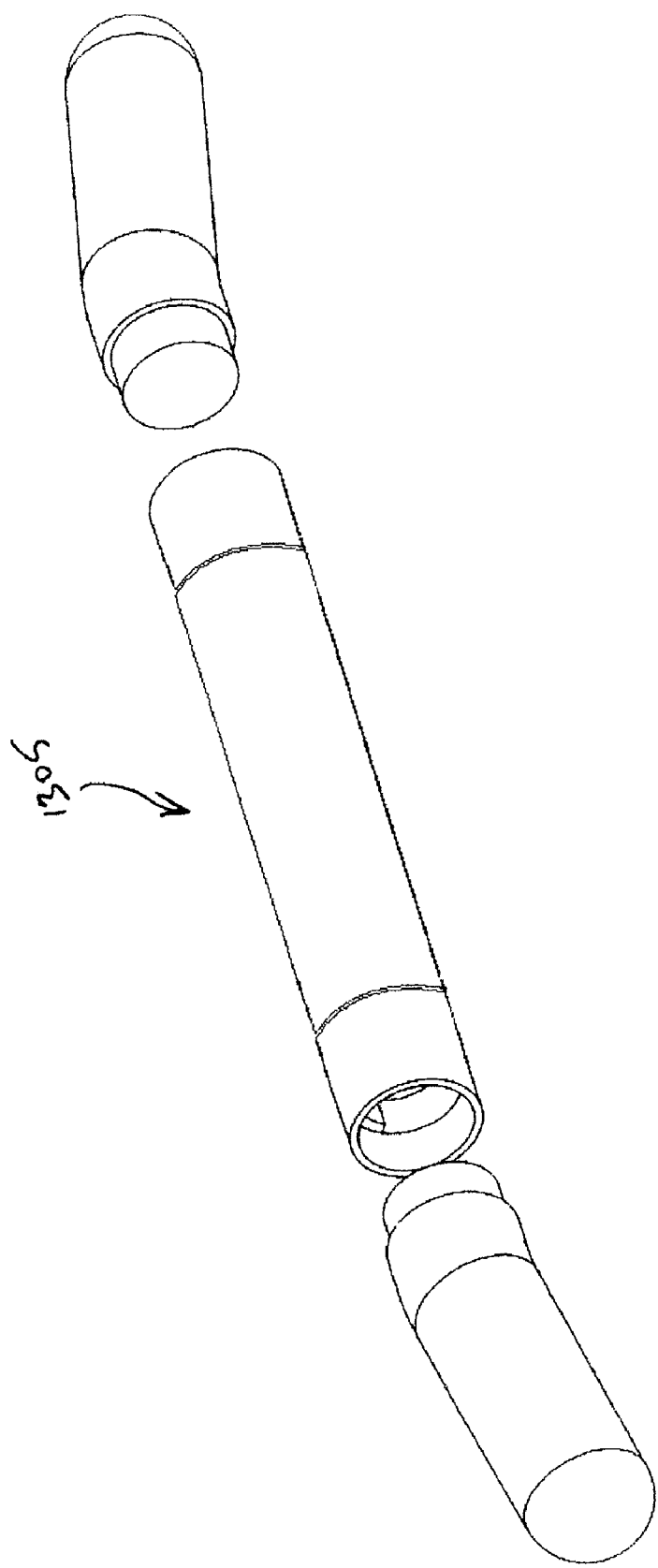
FIG. 13 shows another embodiment of an articulating rod.
Figure 14:
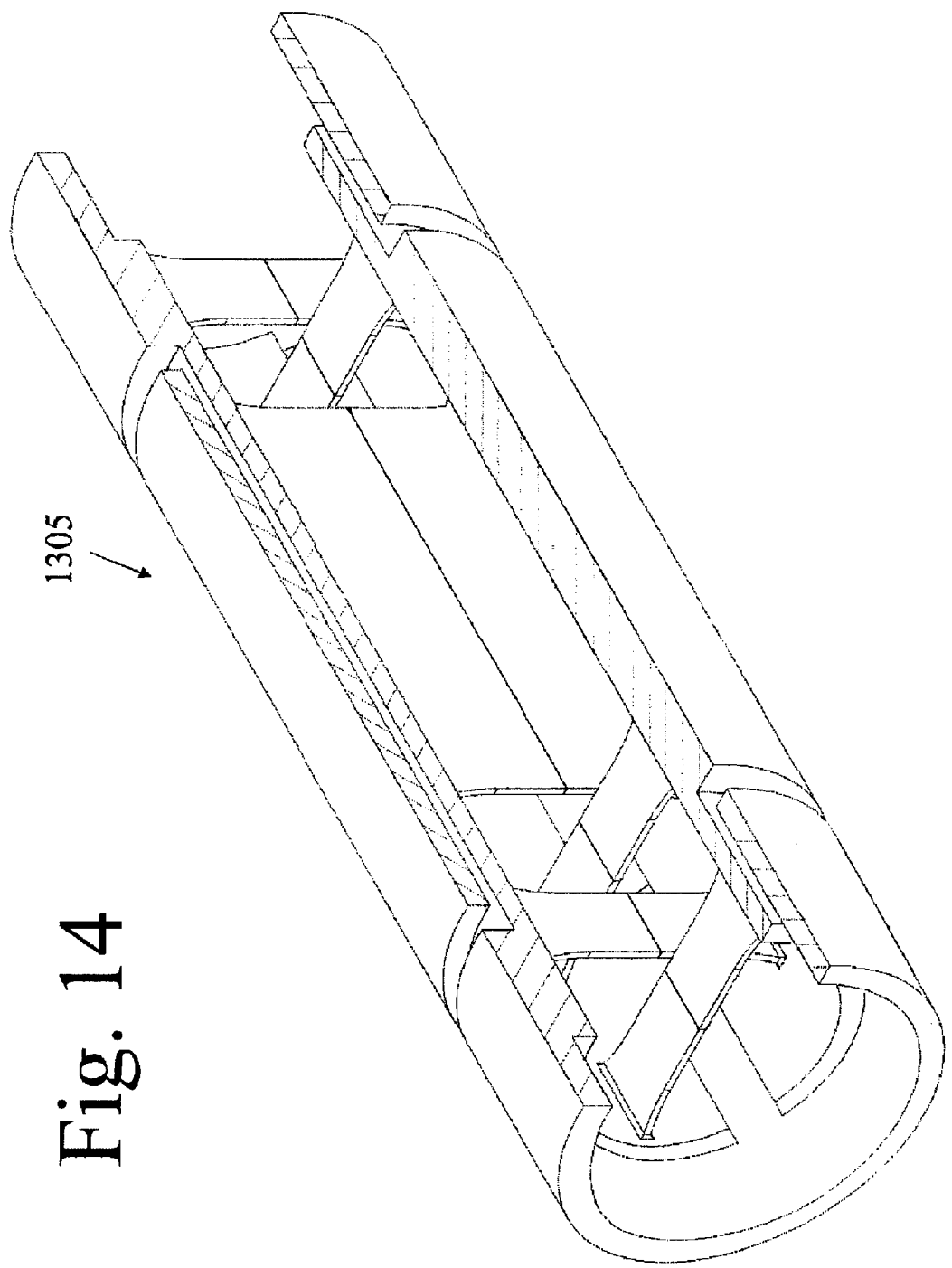
FIG. 14 shows an articulating member of the rod.

FIG. 11 shows another embodiment of an articulating rod 1105 in an exploded state. The rod 1105 includes five sections that are interconnected to one another and that can articulate relative to one another. The rod 1105 includes a pair of articulating members 1110 that interconnect the rigid rod sections. With reference to FIGS. 12A and 12B, each of the articulating members 1110 is formed of a plurality of sections 1210 and 1220. The articulating member permits the attached rod components to rotate along their axes. In one embodiment, the first and second fastener attachment segments (rod components) can rotate relative to one another and where the rotational range is +45 to −45 degrees. The articulating member is a flexure based bearing, utilizing internal flat crossed springs, capsuled in a cylindrical housing, to provide precise rotation with low hysteresis and no frictional losses. The bearing is stiction-free, requires no lubrication, and is self-returning. The articulating member can resist rotational movement away from a neutral state and the extent of resistance to rotation is directly related to the extent of rotation. The extent of resistance to rotation can be a pre-determined property of the device. In one embodiment, the articulation member is has high radial stiffness, high axial stiffness and is frictionless (hence, no particle wear debris). An exemplary articulating member of the type shown in FIGS. 12A and 12B is distributed by Riverhawk Company of N.Y. under the name FREE FLEX PIVOT. FIG. 13 shows another embodiment of the articulating rod having an articulating member 1305 that is constructed in a manner similar to the articulating member 1110. The articulating member permits the rod sections to rotate along their axes. FIG. 14 shows a cross-sectional view of the articulating member 1305, which comprises several sections formed of a plurality of internal, interconnected structures that are adapted to move and/or deform relative to one another.

FIG. 15A shows articulating rods of FIGS. 11 and 13 being used to interconnect the screws on each side of the midline of the same vertebral bodies. FIG. 15A shows an articulating rod in combination with a rigid screw and rod. The rigid screw and rod form a cantilever framework that is attached to the stable segment. Dynamic screws are then anchored into the vertebral bodies with abnormal alignment and/or motion and attached to the rigid rod. In this way, the degenerated segments are stabilized while motion is preserved. In the embodiments of FIG. 15, there is shown a first fastener and a second fastener attached at one end onto a posterior aspect of a first vertebra, wherein the fasteners are positioned on opposite sides of the vertebral midline. A housing is attached to another end of each fastener and adapted to transition between a first and second state, wherein the housing and fastener are freely movable relative to one another in a first state and immobilized relative to one another in a second state. A device of FIG. 11 is adapted to attach onto a housing and fastener at one end and a second housing and fastener at another end, wherein the body of the device forms a first platform P1 that crosses the midline of vertebra V1. A rigid device as shown above can be attached to a second vertebra V2 and forms a second platform P2 that crosses the midline of vertebral V2. An inter-connector L can be rigidly affixed onto each of platforms P1 and P2 and form a cantilever support structure, wherein vertebra V2 forms the construct's stable base of support and upon which a mobile vertebra V1 is anchored.

The preceding disclosure provides a method through which alignment may be corrected and motion may be preserved even in those degenerated segments that currently require fusion and complete immobilization. In this method, a rigid screw and rod are used as a cantilever framework onto which other vertebral segments can be attached using dynamic connectors. Depending on the anchor site, the dynamic connectors can be attached on one side of the rigid anchor or on both sides of it. In the cervical spine, for example, stability can be provided to a large segment of the neck by placement of a rigid bone screw in an intermediate level (usually C5) and then connecting it to a rigid rod. This forms a cantilever framework onto which dynamic anchors can be attached. The dynamic screws are attached to an upper level (usually C2) and a lower level (usually C7 or T1) and, collectively, the construct provides effective stabilization of the neck while preserving motion.

This method can be alternatively applied using a rod capable of movement along its long axis, such as a rod with an articulating member. When employed, the rod would retain the cantilever framework needed for stabilization but provide an extended range of motion during movement. It should be appreciated that the rigid and dynamic screws disclosed are illustrative and that the method itself can be used with any rigid and dynamic fasteners.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. An orthopedic assembly, comprising:
a bone fixation assembly having a bone anchor adapted to be secured to a first skeletal member and a housing member having a rod member-receiving portion that receives an elongated rod member, wherein the bone fixation assembly contains a deployable locking mechanism that is adapted to reversibly affix the elongated rod member onto the rod member receiving portion;
the elongated rod member being comprised of at least one rod member and at least one rotational flexure bearing wherein the at least one rod member and the at least one rotational flexure bearing are coaxially aligned along a central axis, wherein the elongated rod member extends from a proximal end along the central axis for a total length of a first distance, wherein the flexure bearing extends along the central axis for a second distance, and wherein the first distance is greater than the first distance;
the flexure bearing having at least a first and second cylindrical member, wherein each cylindrical member has an outer cylindrical surface and a concentric internal cylindrical surface, wherein the first and second cylindrical members are coaxially aligned, and wherein the first and second cylindrical members can rotate relative to one another along the central axis;
wherein the first and second cylindrical members are joined by at least one spring member that extends from the internal concentric surface of the first cylindrical member to the internal concentric cylindrical surface of the second cylindrical member and wherein the first cylindrical member is separated from direct threaded engagement with the second cylindrical member.

2. An assembly as in claim 1, wherein a first portion of the elongated rod member is attached to a first bone fixation assembly and a second portion of the elongated rod member is attached to a second bone fixation assembly.

3. An assembly as in claim 2, wherein both fixation assemblies are affixed on opposite sides of the vertebral midline of the same vertebral bone and wherein the elongated rod member is adapted to reconstruct a removed segment of the vertebral lamina.

4. An assembly as in claim 2, wherein the assembly is adapted to attach onto a first skeletal member and further comprising:
a second assembly as in claim 2, wherein the second assembly is adapted to attach onto a second skeletal member; and
an orthopedic implant connecting the first and second assemblies.

5. An assembly as in claim 1, wherein the flexure bearing permits a first portion of the elongated rod member to rotate relative to a second portion of the elongated rod member about the central axis of the elongated rod member.

6. An orthopedic assembly as in claim 5, wherein the extent of rotation between the first and second cylindrical member is less than +/−45 degrees.

7. An orthopedic assembly as in claim 1, wherein a second orthopedic implant is attached onto a segment of the elongated rod member.

8. An orthopedic assembly as in claim 4, wherein movement between the first and second skeletal segments produces rotational movement between the first and second cylindrical member of the rotational flexure bearing of an affixed elongated rod member.

9. An orthopedic assembly as in claim 8, wherein movement between the first and second skeletal segments is resisted by the deformation of the at least one spring member that attach the internal concentric surfaces of the first and second cylindrical member of the rotational flexure bearing.

10. An orthopedic assembly as in claim 1, wherein the at least one spring member that extends from the internal concentric surface of the first cylindrical member to the internal concentric cylindrical surface of the second cylindrical member of the rotational flexure bearing provide high axial stiffness and minimal movement of the first and second cylindrical members relative to one another along the central axis of the flexure bearing.

11. An orthopedic assembly as in claim 1, wherein the at least one spring member that extends from the internal concentric surface of the first cylindrical member to the internal concentric cylindrical surface of the second cylindrical member resists rotational movement of the first and second cylindrical members segments away from a neutral state and extent of resistance is directly related to the extent of rotation between the cylindrical members.

12. An orthopedic assembly adapted to provide movement between adjacent skeletal segments, comprising:
a bone fixation member having a bone anchor adapted to be secured to a first skeletal member and a housing assembly having a rod member receiving portion that receives an elongated rod member, wherein the bone fixation member contains a deployable locking mechanism that is adapted to reversibly affix the elongated rod member onto the rod member receiving portion;
the elongated rod member being received within the rod member-receiving portion of the fixation member, wherein the elongated rod member comprises at least one rod member and at least one rotational flexure bearing that are coaxially aligned along a central axis, wherein the elongated rod member extends from a proximal end along the central axis for a total length of a first distance, wherein the flexure bearing extends along the central axis for a second distance, and wherein the first distance is greater than the first distance;
the flexure bearing having at least a first and second cylindrical member, wherein each cylindrical member has an outer cylindrical surface and a concentric internal cylindrical surface, wherein the first and second cylindrical members are coaxially aligned, and wherein the first and second cylindrical members can rotate relative to one another along the central axis;

the first and second cylindrical members being further joined by at least one spring member that extends form the internal concentric cylindrical surface of the first cylindrical member to the internal concentric cylindrical surface of the second cylindrical member;

wherein the spring member resists relative rotation of the first and second cylindrical members along the central axis away from a neutral rotation position in a rotational direction, wherein an extent of resistance to rotation increases with an extent of rotation of the first cylindrical member relative to the second cylindrical member in a direction away from the neutral rotation position and wherein the spring member returns the first and second cylindrical members to the neutral rotation position after dissipation of a force that produces the relative rotation of the cylindrical members.

13. An assembly as in claim 12, wherein a first portion of the elongated rod member is attached to a first bone fixation assembly and a second portion of the elongated rod member is attached to a second bone fixation assembly.

14. An assembly as in claim 13, wherein both fixation assemblies are affixed on opposite sides of the vertebral midline of the same vertebral bone and wherein the elongated rod member is adapted to reconstruct a removed segment of the vertebral lamina.

15. An orthopedic assembly as in claim 12, wherein the extent of rotation between the first and second cylindrical member is less than +/−45 degrees.

16. An assembly as in claim 13, wherein the assembly is adapted to attach onto a first skeletal member and further comprising:
a second assembly as in claim 13, wherein the assembly is adapted to attach onto a second skeletal member; and
an orthopedic implant connecting the first and second assemblies.

17. An orthopedic assembly as in claim 16, wherein movement between the first and second skeletal segments produces rotational movement between the first and second cylindrical member of the rotational flexure bearing of an affixed elongated rod members.

18. An orthopedic assembly as in claim 17, wherein movement between the first and second skeletal segments is resisted by the deformation of the at least one spring member that attach the internal concentric surfaces of the first and second cylindrical member of the rotational flexure bearing.

19. An orthopedic assembly as in claim 12, wherein the at least one spring member that extends from the internal concentric surface of the first cylindrical member to the internal concentric cylindrical surface of the second cylindrical member of the rotational flexure bearing provide high axial stiffness and minimal movement of the first and second cylindrical members relative to one another along the central axis of the flexure bearing.

* * * * *